United States Patent [19]

Hengartner et al.

[11] Patent Number: 4,680,310
[45] Date of Patent: Jul. 14, 1987

[54] TETRAHYDRONAPHTHALENE DERIVATIVES

[75] Inventors: Urs Hengartner, Basel; Henri Ramuz, Birsfelden, both of Switzerland

[73] Assignee: Hoffmann-La Roche Inc., Nutley, N.J.

[21] Appl. No.: 786,253

[22] Filed: Oct. 10, 1985

[30] Foreign Application Priority Data

Oct. 11, 1984 [CH] Switzerland .................. 4870/84

[51] Int. Cl.$^4$ .................. H61K 31/24; C07D 317/44; C07D 319/14; C07C 149/20; C07C 69/00; C07C 39/17; C07C 43/18; C07B 93/08

[52] U.S. Cl. .................................. 514/539; 514/475; 514/512; 514/518; 514/524; 514/654; 514/682; 514/721; 514/732; 549/359; 549/362; 549/433; 549/437; 549/440; 549/443; 558/58; 558/269; 560/152; 560/153; 560/154; 564/355; 564/360; 568/632; 568/633; 568/634; 568/736

[58] Field of Search .................. 560/152, 153, 154; 549/359, 362, 433, 437, 443, 440; 514/475, 524, 512, 518, 539, 654, 721, 732, 682; 564/355, 360; 568/633, 632, 634, 736; 558/58, 269

[56] References Cited

U.S. PATENT DOCUMENTS

3,957,845 5/1976 Trelber et al. .................. 514/524 X
4,127,588 11/1978 Ramuz .................. 549/359 X

FOREIGN PATENT DOCUMENTS

913199 9/1970 Fed. Rep. of Germany .
69029899 10/1970 Japan .
1256753 12/1971 United Kingdom .

*Primary Examiner*—Werren B. Lone
*Assistant Examiner*—Vera C. Clarke

*Attorney, Agent, or Firm*—Jon S. Saxe; Bernard S. Leon; Matthew Boxer

[57] ABSTRACT

Tetrahydronaphthalene derivatives of the formula

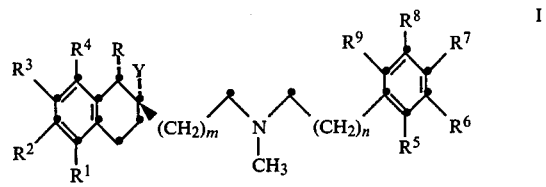

wherein Y, m, n, R and $R^1$ to $R^9$ are as set forth herein, are described.

These compounds have a pronounced calcium-antagonistic and anti-arrhythmic activity and can accordingly be used as medicaments, especially for the control or prevention of angina pectoris, ischaemia, arrhythmias and high blood pressure. The compounds of formula I can be prepared by the amination of a compound of the formula

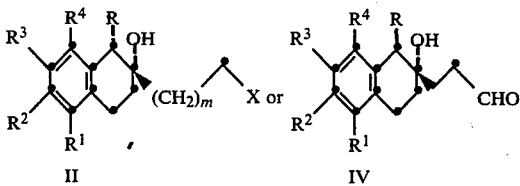

with a corresponding N-methyl-phenylalkylamine and optional subsequent O-acylation. Compounds of formula II and IV are also described and are within the scope of the invention.

36 Claims, No Drawings

TETRAHYDRONAPHTHALENE DERIVATIVES

BRIEF SUMMARY OF THE INVENTION

The invention relates to tetrahydronaphthalene derivatives. In particular, it relates to tetrahydronaphthalene derivatives of the formula

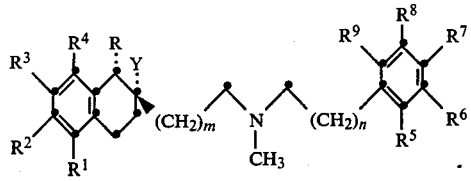

wherein R is hydrogen or lower-alkyl, $R^1$, $R^2$, $R^3$ and $R^4$ each independently is hydrogen, halogen or lower-alkoxy or two adjacent residues together are methylenedioxy or ethylenedioxy, $R^5$, $R^6$, $R^7$, $R^8$ and $R^9$ each independently is hydrogen, halogen, $C_1$–$C_{10}$-alkoxy, lower alkylthio, lower-alkoxy-lower-alkoxy or $\omega,\omega,\omega$-trifluoro-lower-alkoxy or two adjacent residues together are methylenedioxy or ethylenedioxy, Y is hydroxy, lower-alkylcarbonyloxy, lower-alkoxy-lower-alkylcarbonyloxy, lower-alkoxycarbonyloxy, lower-alkoxy-lower-alkoxycarbonyloxy, lower-alkylthio-lower-alkylcarbonyloxy or optionally substituted benzylcarbonyloxy, m is the number 1 or 2 and n is the number 1, 2 or 3,
in the form of racemates and optical antipodes, as well as pharmaceutically usable acid addition salts thereof.

These compounds have valuable pharmacodynamic properties.

Objects of the invention are compounds of formula I per se and for use as therapeutically active substances, the preparation of these compounds, intermediates for the preparation of these compounds, medicaments containing these compounds and the preparatiion of such medicaments, as well as the use of compounds of formula I in the control or prevention of illnesses or in the improvement of health, especially in the control or prevention of angina pectoris, ischaemia, arrhythmias and high blood pressure.

DETAILED DESCRIPTION OF THE INVENTION

The term "lower-alkyl" used in the present description—alone or in combination—denotes straight-chain and branched, saturated hydrocarbon residues with 1–6, preferably 1–4, carbon atoms such as methyl, ethyl, n-propyl, isopropyl, n-butyl, isobutyl, sec.-butyl, tert.-butyl and the like. The term "lower-alkoxy" denotes lower-alkyl ether groups in which the term "lower-alkyl" is as described above. The term "$C_1$–$C_{10}$-alkoxy" denotes alkyl ether groups in which alkyl has 1–10 carbon atoms. The term "halogen" denotes the four halogen atoms fluorine, chlorine, bromine and iodine. The term "substituted benzylcarbonyloxy" denotes benzylcarbonyloxy groups in which one or two hydrogen atoms is/are replaced by lower-alkyl, lower-alkoxy, halogen or nitro. The term "leaving group" denotes known groups such as halogen, preferably chlorine or bromine, arylsulfonyloxy such as, for example, tosyloxy, bromobenzenesulfonyloxy, benzenesulfonyloxy or mesitylenesulfonyloxy, or alkylsulfonyloxy such as, for example, mesyloxy or trifluoromethylsulfonyloxy.

The invention relates to tetrahydronaphthalene derivatives. In particular, it relates to tetrahydronaphthalene derivatives of the formula

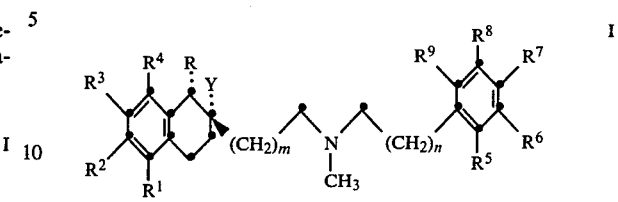

wherein R is hydrogen or lower-alkyl, $R^1$, $R^2$, $R^3$ and $R^4$ each independently is hydrogen, halogen or lower-alkoxy of two of $R^1$, $R^2$, $R^3$ and $R^4$ on adjacent carbon atoms taken together are methylenedioxy or ethylenedioxy, $R^5$, $R^6$, $R^7$, $R^8$ and $R^9$ each independently is hydrogen, halogen, $C_1$–$C_{10}$-alkoxy, lower alkylthio, lower-alkoxy-lower-alkoxy or $\omega,\omega,\omega$-trifluoro-lower-alkoxy or two of $R^5$, $R^6$, $R^7$, $R^8$ and $R^9$ on adjacent carbon atoms taken together are methylenedioxy or ethylenedioxy, Y is hydroxy, lower-alkylcarbonyloxy, lower-alkoxy-lower-alkylcarbonyloxy, lower-alkoxycarbonyloxy, lower-alkoxy-lower-alkoxycarbonyloxy, lower-alkylthio-lower-alkylcarbonyloxy or optionally substituted benzylcarbonyloxy, m is the number 1 or 2 and n is the number 1, 2 or 3,
in the form of racemates and optical antipodes, as well as pharmaceutically usable acid addition salts thereof.

These compounds have valuable pharmacodynamic properties.

Objects of the invention are compounds of formula I per se and and for use as therapeutically active substances, the preparation of these compounds, intermediates for the preparation of these compounds, medicaments containing these compounds and the preparation of such medicaments, as well as the use of compounds of formula I in the control or prevention of illnesses or in the improvement of health, especially in the control or prevention of angina pectoris, ischaemia, arrhythmias and high blood pressure.

Those compounds of formula I in which R is lower-alkyl, particularly isopropyl, are preferred. Y preferably is hydroxy, lower-alkylcarbonyloxy, particularly acetoxy, or lower-alkoxy-lower-alkyl-carbonyloxy, particularly methoxyacetoxy, m and n preferably are the number 1. Further, there are preferred those compounds of formula I in which two of the substituents $R^1$, $R^2$, $R^3$ and $R^4$ are hydrogen and the other two each independently are hydrogen, halogen or lower-alkoxy. Those compounds of formula I in which $R^1$ and $R^4$ each is hydrogen and $R^2$ and $R^3$ each is lower-alkoxy or $R^2$ is halogen and $R^3$ is hydrogen are especially preferred. Likewise preferred are the compounds of formula I in which two of the substituents $R^5$, $R^6$, $R^7$, $R^8$ and $R^9$ are hydrogen and the other three each independently is hydrogen, halogen, $C_1$–$C_{10}$-alkoxy, lower-alkylthio or lower-alkoxy-lower-alkoxy. Especially preferred are the compounds in which $R^8$ and $R^9$ each is hydrogen and $R^5$ is hydrogen or $C_1$–$C_{10}$-alkoxy, $R^6$ is hydrogen, $C_1$–$C_{10}$-alkoxy or lower-alkoxy-lower-alkoxy and $R^7$ is hydrogen, halogen, $C_1$–$C_{10}$-alkoxy, lower-alkylthio or lower-alkoxy-lower-alkoxy.

From the above it follows that there are particularly preferred those compounds of formula I in which R is isopropyl, Y is hydroxy, acetoxy or methoxyacetoxy, $R^1$, $R^4$, $R^8$ and $R^9$ each is hydrogen, $R^2$ and $R^3$ each is lower-alkoxy or $R^2$ is halogen and $R^3$ is hydrogen. $R^5$ is hydrogen or $C_1$–$C_{10}$-alkoxy, $R^6$ is hydrogen, $C_1$–$C_{10}$-alkoxy or lower-alkoxy-lower-alkoxy, $R^7$ is hydrogen, halogen, $C_1$–$C_{10}$-alkoxy, lower-alkylthio or lower-alkoxy-lower-alkoxy and m and n each is the number 1.

Most preferred compounds of formula I are:

2-[2-[(3,4-Dimethoxyphenethyl)methylamino]ethyl]-6-fluoro-1,2,3,4-tetrahydro-1α-isopropyl-2α-naphthyl methoxyacetate, 6,7-dimethoxy-2-[2-[(3,4-dimethoxyphenethyl)methylamino]ethyl]-1,2,3,4-tetrahydro-1α-isopropyl-2α-naphthyl methoxyacetate, 6,7-dimethoxy-2-[2-[(3,4-dimethoxyphenethyl)methylamino]ethyl]-1,2,3,4-tetrahydro-1α-isopropyl-2α-naphthyl acetate and

[1S,2S]-2-[2-[(3,4-dimethoxyphenethyl)methylamino]ethyl]-6-fluoro-1,2,3,4-tetrahydro-1-isopropyl-2-naphthyl methoxyacetate.

Other exemplary compounds of formula I are:

6-chloro-2-[2-[(3,4-dimethoxyphenethyl)methylamino]ethyl]1,2,3,4-tetrahydro-1α-isopropyl-2α-naphthylmethoxyacetate;

6-fluoro-1,2,3,4-tetrahydro-1α-isopropyl-2-[2-[(3-(2,2,2-trifluoroethoxy)phenethyl)methylamino]ethyl]-2α-naphthyl acetate; and 5,8-dimethoxy-2-[2-[(3,4-dimethoxyphenethyl)methylamino]ethyl]-1,2,3,4-tetrahydro-2-napthyl acetate.

The compounds of formula I in the form of racemates and optical antipodes, as well as pharmaceutically usable or acceptable acid addition salts thereof can be prepared as follows:

(a) for compounds of formula I in which Y is hydroxy, reacting a compound of the formula

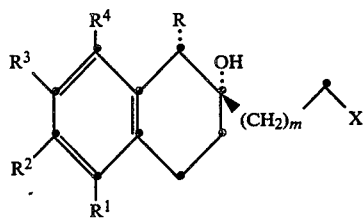

II wherein X is a leaving group and R, $R^1$, $R^2$, $R^3$, $R^4$ and m are as described above, with an amine of the formula

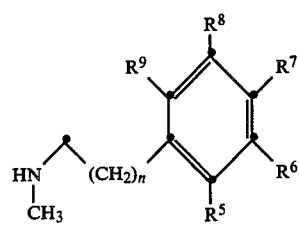

III wherein $R^5$, $R^6$, $R^7$, $R^8$, $R^9$ and n are as described above, or (b) for compounds of formula I in which Y is hydroxy and m is the number 2, reductively aminating an aldehyde of the formula

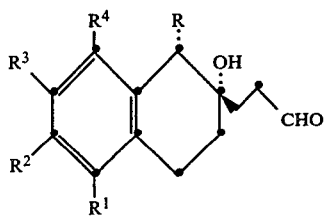

IV wherein R, $R^1$, $R^2$, $R^3$ and $R^4$ are as described above, with an amine of formula III above, or (c) for the preparation of compounds of formula I in which Y is lower-alkylcarbonyloxy, lower-alkoxy-lower-alkylcarbonyloxy, lower-alkoxycarbonyloxy, lower-alkoxy-lower-alkoxycarbonyloxy, lower-alkylthio-lower-alkylcarbonyloxy or optionally substituted benzylcarbonyloxy reacting a compound of the formula

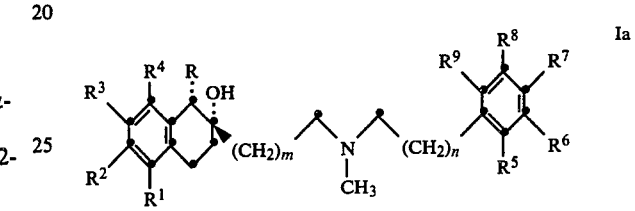

Ia wherein R, $R^1$, $R^2$, $R^3$, $R^4$, $R^5$, $R^6$, $R^7$, $R^8$, $R^9$ m and n are as described above,
with an acylating agent yielding a lower-alkylcarbonyl, lower-alkoxy-lower-alkylcarbonyl, lower-alkoxycarbonyl, lower-alkoxy-lower-alkoxycarbonyl, lower-alkylthio-lower-alkylcarbonyl or optionally substituted benzylcarbonyl group, and (d) if desired, resolving a racemate obtained into the optical antipodes, and/or (e) converting a compound obtained into a pharmaceutically usable or acceptable acid addition salt.

A compound of formula II is reacted with an amine of formula III according to methods known per se. The reaction is carried out in the presence or absence of an organic solvent which is inert under the reaction conditions at a temperature between about 20° and 150° C., preferably between about 80° and 120° C. Solvents such as dimethylformamide, dimethyl sulfoxide, alcohols such as isopropanol or tert.-butanol, ethers such as tetrahydrofuran or dioxan, aromatic hydrocarbons such as benzene, toluene or xylene, chlorinated hydrocarbons such as methylene chloride, carbon tetrachloride or chlorobenzene, and the like come into consideration in this reaction. The reaction is advantageously carried out in the presence of an acid-binding agent, for example a tertiary amine such as trimethylamine, triethylamine, ethyldiisopropylamine or 1,5-diazabicyclo[4.3.0]-non-5-ene, whereby excess amine of formula III can serve as the acid-binding agent. For reasons of convenience the reaction is carried out at atmospheric pressure, although higher pressure can also be used.

The reductive amination of a compound of formula IV is also carried out in a manner known per se by reaction with an amine of formula III in the presence of a reduction agent such as sodium cyanoborohydride or hydrogen/catalyst in a solvent, for example an alcohol or an aqueous alcohol such as methanol, ethanol or propanol or aqueous solutions thereof. For reasons of convenience the reductive amination is carried out at atmospheric pressure, although it can also be carried out at elevated pressures, especially when hydrogen/catalyst is used as the reduction agent. Suitable catalysts are, in particular, Raney-nickel and palladium. The reaction temperature lies, depending on the reduction agent used, between about 0° and 50° C. for sodium cyanoborohydride and between about 0° and 100° C. for hydrogen/catalyst.

The acylation of a compound of formula Ia is also carried out according to methods known per se. Suitable acylating agents are, in particular, activated acid derivatives such as acid halides and acid anhydrides or mixed acid anhydrides. The reaction is carried out in an organic solvent or solvent mixture which is inert under the reaction conditions at a temperature between about 0° C. and the reflux temperature. As solvents there come into consideration, in particular, aromatic hydrocarbons such as benzene, toluene or xylene, chlorinated hydrocarbons such as methylene chloride or chloroform, ethers such as diethyl ether, tetrahydrofuran or dioxane, and the like.

The compounds of formula III are known or can be prepared according to known procedures.

The starting materials of formulae II and IV are also within the scope of the invention. A process for their preparation is outlined in Scheme I hereinafter. With respect to the precise reaction conditions, reference is made to the experimental section.

Scheme I

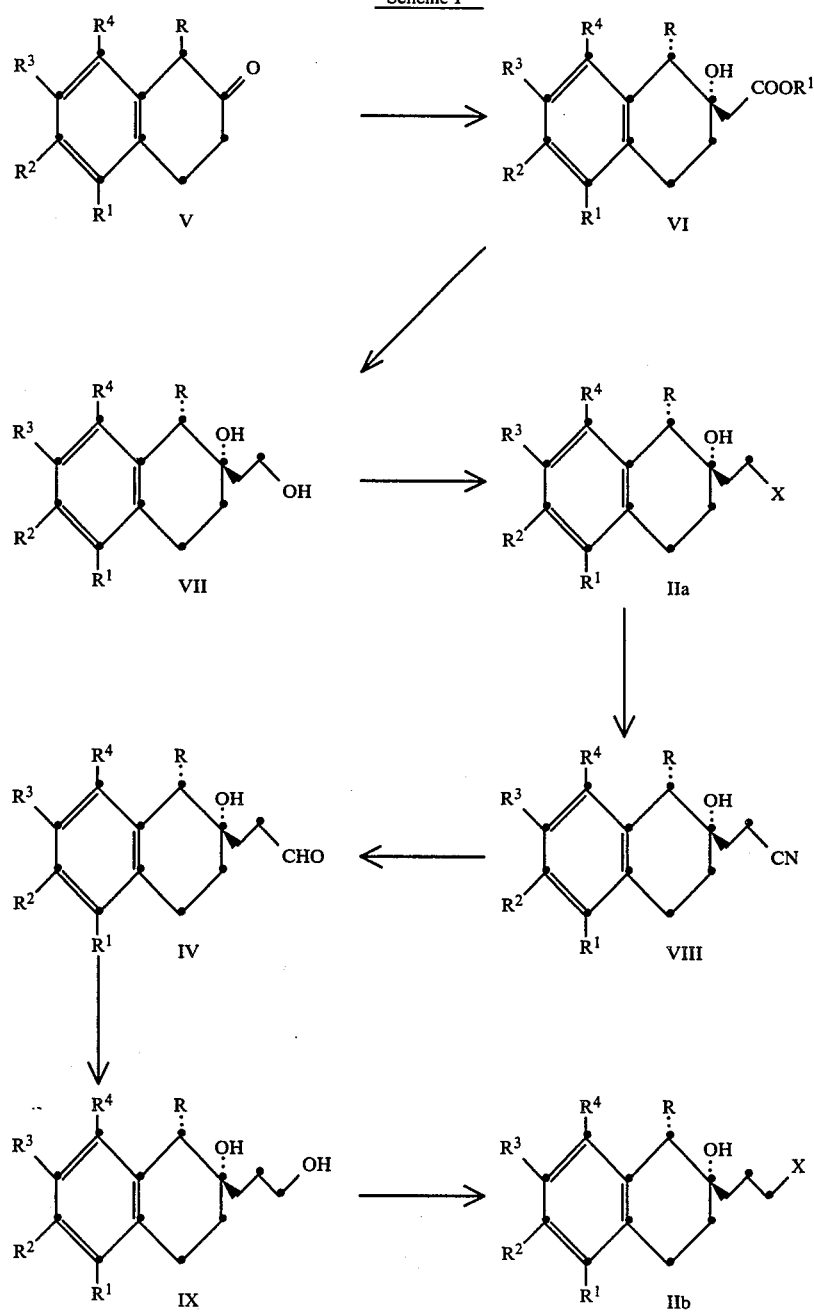

wherein R, $R^1$, $R^2$, $R^3$, $R^4$ and X are as described above and $R^{10}$ is hydrogen or lower-alkyl.

In the first step a tetralone derivative of formula V is reacted with an alkyl haloacetate in the presence of zinc in a manner known per se, whereby the reaction with a tert.-butyl haloacetate can also be carried out in the presence of magnesium. The reaction is carried out in an inert organic solvent or solvent mixture, for example an ether such as diethyl ether or tetrahydrofuran or an aromatic hydrocarbon such as benzene or toluene or mixtures thereof, at a temperature between about 0° C. and the reflux temperature of the solvent. In situ decomposition of the addition product formed as as an intermediate yields an ester of formula VI which can be hydrolyzed in a manner known per se to the corresponding acid of formula VI.

An ester or an acid of formula VI can also be reduced according to known methods to the corresponding alcohol of formula VII. Suitable reduction agents are, for example, lithium aluminum hydride, sodium bis-(2-methoxyethoxy)aluminum dihydride, lithium borohydride, diisobutylaluminum hydride or diborane and the like. The reduction is carried out in an organic, aprotic solvent which is inert under the reaction conditions, for example an ether such as diethyl ether, tetrahydrofuran or dioxan, a hydrocarbon such as hexane or cyclohexane or an aromatic hydrocarbon such as benzene or toluene, and the like, at a temperature between about room temperature and 100° C., preferably between about room temperature and 50° C.

An alcohol of formula VII can then be converted by reaction with an aryl- or alkylsulfonyl halide in a known manner into a compound of formula IIa in which X is an aryl- or alkylsulfonyl group. This reaction is advantageously carried out in the presence of an acid-binding agent, for example a tertiary amine such as triethylamine, ethyldiisopropylamine or pyridine, in the presence or absence of an organic solvent which is inert under the reaction conditions at a temperature between about 0° and 80° C. As solvents there come into consideration ethers such as diethyl ether, tetrahydrofuran or dioxan, aromatic hydrocarbons such as benzene or toluene, chlorinated hydrocarbons such as methylene chloride or chloroform, and the like, mixtures thereof or excess acid-binding agent. A compound of formula IIa in which X is halogen is conveniently obtained by reacting a compound of formula IIa in which X is aryl- or alkylsulfonyl with a sodium halide in acetone or a pyridine hydrohalide at a temperature between about 0° and 100° C.

A compound of formula IIa is then converted into a compound of formula VIII according to known methods by reaction with sodium or potassium cyanide. The reaction with the cyanide is carried out in an organic solvent which is inert under the reaction conditions such as dimethyl sulfoxide, dimethylformamide, hexamethylphosphoric acid triamide and the like at a temperature between about room temperature and 150° C., preferably between about 40° and 80° C.

A compound of formula VIII can thereafter be reduced to a compound of formula IV according to known methods. Suitable reduction agents for this step are, for example, sodium bis-(2-methoxyethoxy)aluminum dihydride, diisobutylaluminum hydride and the like. The reduction is carried out in an organic solvent which is inert under the reaction conditions, for example a chlorinated hydrocarbon such as methylene chloride, an ether such as diethyl ether, tetrahydrofuran or dioxan, a hydrocarbon such as hexane or cyclohexane, and the like, at a temperature between about 20° and 100° C., preferably between about 30° and 50° C.

A compound of formula IV can then be reduced further to the corresponding alcohol of formula IX which, in turn, can then be converted into the compound of formula IIb in an analogous manner to that given above for the conversion VII→IIa. The reduction of a compound of formula IV is carried out in a manner known per se with reduction agents which are usual for such a reduction, for example hydrogen in the presence of a catalyst such as Raney-nickel or palladium, lithium aluminum hydride, sodium borohydride or lithium borohydride and the like, in an organic solvent which is inert under the reaction conditions, for example an ether such as diethyl ether or tetrahydrofuran, an alcohol such as methanol or ethanol, and the like, at a temperature between about 20° and 100° C.

The compounds of formulae VI, VII, VIII and IX are also within the scope invention, while the tetralone derivatives of formula V are either known or can be obtained in analogy to the preparation of the known compounds.

From the above it follows that compounds of the formula

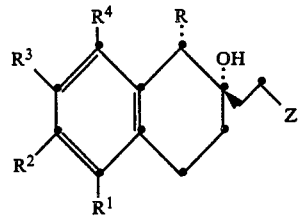

wherein R is hydrogen or lower-alkyl, $R^1$, $R^2$, $R^3$ and $R^4$ each independently is hydrogen, halogen or lower-alkoxy or two of $R^1$, $R^2$, $R^3$ and $R^4$ on adjacent carbon atoms taken together are methylenedioxy or ethylenedioxy and Z is hydroxy, hydroxymethyl, formyl, cyano, a leaving group or the group —$CH_2$—X in which X is a leaving group; are within the scope of the invention.

The compounds of formula I contain at least one asymmetric centre (2-position) and can therefore exist as optical antipodes or as racemates. Accordingly, the invention relates to a compound of formula I; its optical antipode, or a racemate thereof.

For any compound named herein, such as a compound of Formula I, which has at least one asymmetric center, where the name does not indicate a particular optical antipode, the racemate is intended.

The compounds of formula I, form pharmaceutically usable or acceptable acid addition salts with pharmaceutically usable or acceptable inorganic acids, for example with hydrohalic acids such as hydrochloric acid or hydrobromic acids, or with other mineral acids, such as, sulfuric acid or phosphoric acid, and with organic acids, for example tartaric acid and maleic acid. The preferred salts are the hydrohalides, especially the hydrochlorides. Compounds of formula I which contain more than one asymmetric centre are present in the relative configuration indicated by formula I.

The compounds of formula I have a pronounced calcium-antagonistic activity and can accordingly be used as medicaments, especially for the control or prevention of angina pectoris, ischaemia, arrhythmias and high blood pressure.

The calcium-antagonistic activity as well as the blood pressure-lowering properties of the compounds in accordance with the invention can be demonstrated in the tests described hereinafter:

A. $^3$H-Nifedipine binding determinations:

The determination is carried out on homogenates or on partially-cleaned membranes of rabbit or guinea pig heart. The reaction mixture (0.3 ml) consists of 0.2–0.8 mg of membrane protein, 1 nM of $^3$H-nifedipine (or 0.25 nM of $^3$H-nitrendipine) and various concentrations of the test substances. The incubation lasts 30 minutes at 25° C. or 37° C. and is stopped by dilution with the incubation buffer; a filtration is subsequently carried out. The filter-bound radioactivity is measured with a scintillation counter. Specific binding (i.e. receptor-bound) is defined as the differences between total and unspecific-bound radioactivity. The unspecific binding is determined in the presence of an excess of non-radioactive nifedipine (1 μM).

The activity (potency) of a compound in this test is defined by the $IC_{50}$ and % maximum inhibition values (% max. inhibition). The $IC_{50}$ is the substance concentration (in mol/l) which produces a half-maximum inhibition of the specific $^3$H-nifedipine (or $^3$H-nitrendipine) binding. The maximum inhibition of the specific binding is given by the % maximum inhibition value; this value is established as 100% for the reference compound nifedipine. Both parameters are extrapolated from a concentration-binding curve.

B. Coronary artery strips of dogs:

C. Haemodynamic parameters in the narcotized dog:

The 4 most important measurement parameters (with respective measurement units) of the haemodynamic experiment are: (1) CBF: Coronary Blood Flow (in ml/min)—the velocity of blood flow through the coronary arteries; (2) HR: heart rate (in beats/min)—the heart frequency; (3) BP: blood pressure (in mm Hg)—the blood pressure; and (4) dp/dt: rate of increase in left ventricular pressure (in mm Hg/sec) as a measurement of the contractility force of the heart. The values are given as the % maximum variation from the initial value (Δ%) per dosage administered.

There is thus obtained not only an overall picture of the activity of the substance, but also an estimation as to the potential selectivity for a specific part of the circulatory system in the entire organism. After the administration of an anaesthetic, the dog is intubated and respired artificially. Blood pH, $pCO_2$, $pO_2$ and haemoglobin are measured hourly with a blood-gas analyser. The blood pressure (systolic and diastolic) is measured with a probe in the aorta abdominalis. The heart frequency is recorded by means of a tachometer, which is disengaged from the pressure pulse. For the other measurements the heart must first be opened in order that a probe can be inserted in the left ventricle (heart chamber) for the pressure measurements (dp/dt). The coronary blood flow is measured with a flowing probe in the left coronary artery (descendens).

The results obtained in these tests are compiled in the following Table:

TABLE

| Compound | A | | B | C | | | | Dosage |
| --- | --- | --- | --- | --- | --- | --- | --- | --- |
| | $IC_{50}$ [M] | % max inhib. | $IC_{50}$ [M] | CBF Δ % | HR Δ % | BP Δ % | dp/dt Δ % | mg/kg i.v. |
| A | $5.6 \cdot 10^{-8}$ | 77 | $2.8 \cdot 10^{-9}$ | +93 | −3 | −18 | −5 | 0.1 |
| B | $5.0 \cdot 10^{-9}$ | 100 | $6.1 \cdot 10^{-9}$ | +100 | −20 | −23 | +13 | 0.1 |
| C | $7.0 \cdot 10^{-6}$ | 73 | $7.8 \cdot 10^{-8}$ | +58 | −5 | −16 | +26 | 0.1 |
| D | $5.7 \cdot 10^{-7}$ | 82 | $8.7 \cdot 10^{-8}$ | +58 | −15 | −9 | +3 | 0.1 |
| E | $1.6 \cdot 10^{-7}$ | 88 | $2.0 \cdot 10^{-8}$ | +65 | −7 | −12 | +22 | 0.1 |

A = 2-[2-[(3,4-Dimethoxyphenethyl)methylamino]ethyl]-6-fluoro-1,2,3,4-tetrahydro-1α-isopropyl-2α-naphthyl methoxyacetate
B = [1S,2S]—2-[2-[(3,4-Dimethoxyphenethyl)methylamino]ethyl]-6-fluoro-1,2,3,4-tetrahydro-1-isopropyl-2-naphthyl methoxyacetate
C = [1R,2R]-2-[2-[(3,4-Dimethoxyphenethyl)methylamino]ethyl]-6-fluoro-1,2,3,4-tetrahydro-1-isopropyl-2-napthyl methoxyacetate
D = 6,7-Dimethoxy-2 [2-[(3,4-dimethoxyphenethyl)methylamino]ethyl]-1,2,3,4-tetrahydro-1α-isopropyl-2α-napthyl acetate
E = 6,7-Dimethoxy-[2-[2-[(3,4-dimethoxyphenethyl)methylamino)ethyl]-1,2,3,4-tetrahydro-1α-isopropyl-2α-naphthyl methoxyacetate In this experiment spiral strips (2–2.5 mm wide and 10 mm long) of coronary arteries of dogs are cut and hung up in an organ chamber under an initial tension of 1.5 g. These strips are pre-incubated for a duration of about 1 to 2 hours in Krebs-Henseleit buffer solution which is gassed with Oxycarbon (a mixture of 95% oxygen and 5% carbon dioxide) at 37° C. The relaxing activity of one of these substances is subsequently tested on a KCl (84.7 mM) contracture by the addition of increasing concentrations of the test substance to the organ chamber. The calcium channel-blocking activity of the test substances can therefore be established, as the KCl contracture occurs exclusively by means of calcium flow through the tension-dependent calcium channel.

The activity of a test substance in this test is given by the $IC_{50}$ value. This value is defined as the substance concentration (in mol/l) which produces a half-maximum relaxation of a KCl contracture. This value is also extrapolated from the resulting concentration-activity curve.

The compounds of formula I can be used as medicaments, e.g. in the form of pharmaceutical preparations. The pharmaceutical preparations can be administered orally, e.g. in the form of tablets, coated tablets, dragees, hard and soft gelatine capsules, solutions, emulsions or suspensions. The administration can, however, also be carried out rectally, e.g. in the form of suppositories, or parenterally, e.g. in the form of injection solutions.

For the manufacture of tablets, coated tablets, dragees and hard gelatine capsules the compounds of formula I can be processed with pharmaceutically inert, inorganic or organic excipients. As such excipients there can be used e.g. for tablets, dragees and hard gelatine capsules, lactose, maize starch or derivatives thereof, talc, stearic acid or its salts etc.

Such excipients include pharmaceutically acceptable carrier materials such as water, gelatin, lactose, maize starch or derivatives thereof, polyols, vegetable oils and the like.

For soft gelatine capsules there are suitable as excipients e.g. vegetable oils, waxes, fats, semi-solid and liquid polyols etc.

For the manufacture of solutions and syrups there are suitable as excipients e.g. water, polyols, saccharose, invert sugar, glucose etc.

For injection solutions there are suitable as excipients e.g. water, alcohols, polyols, glycerine, vegetable oils etc.

For suppositories there are suitable as excipients e.g. natural or hardened oils, waxes, fats, semi-liquid or liquid polyols etc.

Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents or antioxidants. They can also contain still other therapeutically valuable substances.

In accordance with the invention compounds of formula I can be used in the control or prevention of angina pectoris, ischaemia, arrhythmias and high blood pressure by administration to warm-blooded animals in need thereof. The dosage can vary within wide limits and will, of course, be adjusted to the individual requirements in each particular case. In general, in the case of oral administration a daily dosage of about 25 to 150 mg of a compound of formula I should be appropriate, whereby, however, the upper limit just given can also be exceeded when this is shown to be indicated.

The following Examples further illustrate the invention. All temperatures are given in degrees Celsius.

EXAMPLE 1

(A) 20.0 g of 2-(6-fluoro-1,2,3,4-tetrahydro-2-hydroxy-1α-isopropyl-2β-naphthyl)ethyl p-toluene-sulfonate and 19.2 g of N-methylhomoveratrylamine were dissolved in 70 ml of anhydrous dimethyl sulfoxide and stirred at 80° for 1 hour. The reaction mixture was poured on to 800 ml of ice-water and extracted with 400 ml of ether. The extract was washed with water, dried over magnesium sulfate and evaporated. The product, purified by column chromatography (silica gel; chloroform/methanol 30:1), was dissolved in ethyl acetate, treated with an excess of hydrogen chloride in ether and again evaporated. The amorphous residue was dissolved in ethyl acetate, treated with ether, seeded and stirred at room temperature overnight. The crystallizate was filtered off, washed with ether and dried. There was obtained 2-[2-[(3,4-dimethoxyphenethyl)methylamino]ethyl]-6-fluoro-1,2,3,4-tetrahydro-1α-isopropyl-2α-naphthalenol hydrochloride. m.p. 190°-192°.

The following compounds were obtained in an analogous manner to that described above by condensation of the substituted 2-(1,2,3,4-tetrahydro-1α-alkyl-2-hydroxy-2β-naphthyl)ethyl p-toluenesulfonates with the corresponding N-methyl-arylalkylamines:

6-Chloro-2-[2-[(3,4-dimethoxyphenethyl)methylamino]ethyl]-1,2,3,4-tetrahydro-1α-isopropyl-2α-naphthalenol hydrochloride, m.p. 195°-198°, 2-[2-[(3,4-dimethoxyphenethyl)methylamino]ethyl]-1,2,3,4-tetrahydro-1α-isopropyl-2α-naphthalenol hydrochloride, m.p. 175°-177°, 6,7-dimethoxy-2-[2-[(3,4-dimethoxyphenethyl)methylamino]ethyl]-1,2,3,4-tetrahydro-1α-isopropyl-2α-naphthalenol, m.p. 119°-120°, 2-[2-[(3,4-dimethoxyphenethyl)methylamino]ethyl]-1,2,3,4-tetrahydro-1α-isopropyl-5,6,7-trimethoxy-2α-naphthalenol hydrochloride, m.p. 170°-172°, 6,7-dimethoxy-2-[2-[[3-(3,4-dimethoxyphenyl)propyl]methylamino]ethyl]-1,2,3,4-tetrahydro-1α-isopropyl-2α-naphthalenol hydrochloride, m.p. 110°-113°, 6-fluoro-1,2,3,4-tetrahydro-1α-isopropyl-2-[2-[(2,4,6-trimethoxyphenethyl)methylamino]ethyl]-2α-naphthalenol hydrochloride, m.p. 146°-148°, 6-fluoro-1,2,3,4-tetrahydro-1α-isopropyl-2-[2-[(3,4,5-trimethoxyphenethyl)methylamino]ethyl]-2α-naphthalenol hydrochloride, m.p. 173°-175°,

[1S,2S]-2-[2-[(3,4-dimethoxyphenethyl)methylamino]ethyl]-6-fluoro-1,2,3,4-tetrahydro-1-isopropyl-2-naphthalenol hydrochloride, m.p. 164°-165°, $[\alpha]_D^{20} = +45.3°$ (c=1, methanol), 2-[2-[(2,5-dimethoxyphenethyl)methylamino]ethyl]-6-fluoro-1,2,3,4-tetrahydro-1α-isopropyl-2α-naphthalenol hydrochloride, m.p. 164°-166°, 6-fluoro-1,2,3,4-tetrahydro-1α-isopropyl-2-[2-[(2-(2,2,2-trifluoroethoxy)phenethyl)methylamino]ethyl]-2α-naphthalenol hydrochloride, m.p. 46°-148°, 6-fluoro-1,2,3,4-tetrahydro-1α-isopropyl-2-[2-[(3-(2,2,2-trifluoroethoxy)phenethyl)methylamino]ethyl]-2α-naphthalenol hydrochloride, 6-fluoro-1,2,3,4-tetrahydro-1α-isopropyl-2-[2-[(3-methoxy-4-(methylthio)phenethyl)methylamino]ethyl]-2α-naphthalenol hydrochloride, m.p. 190°-192°, 6-fluoro-2-[2-[(4-fluorophenethyl)methylamino]ethyl]-1,2,3,4-tetrahydro-1α-isopropyl-2α-naphthalenol hydrochloride, m.p. 148°-150°, 1α-butyl-2-[2-[(3,4-dimethoxyphenethyl)methylamino]ethyl]-6-fluoro-1,2,3,4-tetrahydro-2α-naphthalenol hydrochloride, m.p. 123°-125°, 6-fluoro-1,2,3,4-tetrahydro-1α-isopropyl-2-[2-[(4-methoxyphenethyl)methylamino]ethyl]-2α-naphthalenol hydrochloride, m.p. 123°-125°, 2-[2-[(4-butoxyphenethyl)methylamino]ethyl]-6-fluoro-1,2,3,4-tetrahydro-1α-isopropyl-2α-naphthalenol hydrochloride, m.p. 169°-170° and 2-[2-[(4-decyloxyphenethyl)methylamino]ethyl]-6-fluoro-1,2,3,4-tetrahydro-1α-isopropyl-2α-naphthalenol hydrochloride, m.p. 137°-139°.

The 2-(6-fluoro-1,2,3,4-tetrahydro-2-hydroxy-1α-isopropyl-2β-naphthyl)ethyl p-toluenesulfonate used as the starting material in paragraph (A) was prepared as follows:

(B) 20.0 g of 6-fluoro-1,2,3,4-tetrahydro-2-hydroxy-1α-isopropyl-2β-naphthaleneethanol were dissolved in 140 ml of pyridine and cooled to 0°. After the addition of 18.2 g of p-toluenesulfonyl chloride the mixture was stirred without cooling for 3 hours and then poured into 1 l of water. The product was extracted with 600 ml of ether and the ether extract was washed with 600 ml of 3N aqueous hydrochloric acid, 600 ml of saturated aqueous sodium bicarbonate solution and 600 ml of water. After drying over magnesium sulfate the ether was evaporated off under reduced pressure and the oil remaining behind was recrystallized from 300 ml of cyclohexane. There was obtained 2-(6-fluoro-1,2,3,4-tetrahydro-2-hydroxy-1α-isopropyl-2β-naphthyl)ethyl p-toluenesulfonate, m.p. 91°-92°.

The following compounds were obtained in an analogous manner to that described above by reaction of the corresponding 1,2,3,4-tetrahydro-2-hydroxy-1α-alkyl-2β-naphthaleneethanols with p-toluenesulfonyl chloride:

2-(6-Chloro-1,2,3,4-tetrahydro-2-hydroxy-1α-isopropyl-2β-naphthyl)ethyl p-toluenesulfonate, 2-(1,2,3,4-tetrahydro-2-hydroxy-1α-isopropyl-2β-naphthyl)ethyl p-toluenesulfonate, 2-(6,7-dimethoxy-1,2,3,4-tetrahydro-2-hydroxy-1α-isopropyl-2β-naphthyl)ethyl p-toluenesulfonate, m.p. 74°–75°, 2-(1,2,3,4-tetrahydro-2-hydroxy-1α-isopropyl-5,6,7-trimethoxy-2β-naphthyl)ethyl p-toluenesulfonate, 2-(1α-butyl-6-fluoro-1,2,3,4-tetrahydro-2-hydroxy-2β-naphthyl)ethyl p-toluenesulfonate and

[1S,2S]-2-(6-fluoro-1,2,3,4-tetrahydro-2-hydroxy-1-isopropyl-2-naphthyl)ethyl p-toluenesulfonate, m.p. 66°–67°.

The derivatives which were not crystalline at room temperature were characterized with the aid of spectroscopic methods.

The 6-fluoro-1,2,3,4-tetrahydro-2-hydroxy-1α-isopropyl-2β-naphthaleneethanol used as the starting material in paragraph (B) above was prepared as follows:

(C) A tenth of a solution of 57 g of 6-fluoro-3,4-dihydro-1-isopropyl-2(1H)-naphthalenone and 59.5 g of tert.-butyl bromoacetate in 330 ml of tetrahydrofuran were added to 10.6 g of activated magnesium. After the visually recognizable reaction, brought about by heating, began, the remainder of the solution was added dropwise under reflux within 30 minutes. After completion of the addition, the reaction mixture was heated to reflux for a further 1½ hours. The cooled mixture was treated slowly with a solution of 40 g of ammonium chloride in 400 ml of water and then partitioned between 600 ml of water and 1.5 l of methylene chloride. The organic phase was washed with water, dried over magnesium sulfate and concentrated. After purification by column chromatography (silica gel, hexane/ethyl acetate 5:1) there were obtained tert.-butyl 6-fluoro-1,2,3,4-tetrahydro-2-hydroxy-1α-isopropyl-2β-naphthaleneacetate. The oily product was dissolved in 415 ml of tetrahydrofuran and added dropwise within 30 minutes to a stirred suspension of 13.44 g of lithium aluminum hydride in 400 ml of tetrahydrofuran, whereby the reaction temperature rose to 60°. The mixture was stirred for a further 30 minutes and then cooled to 10°. There are cautiously added in succession 22 ml of water, 22 ml of 28% aqueous sodium hydroxide solution and 66 ml of water. The suspension obtained was filtered, the filter cake was washed with tetrahydrofuran and the filtrate was evaporated. The crystalline residue was recrystallized from 120 ml of cyclohexane. There was obtained 6-fluoro-1,2,3,4-tetrahydro-2-hydroxy-1α-isopropyl-2β-naphthaleneethanol, m.p. 97°–98°.

The following compounds were obtained in an analogous manner to that described above by reaction of the corresponding 3,4-dihydro-1-alkyl-2(1H)-naphthalenones with magnesium/tert.-butyl bromoacetate and subsequent reduction:

6-Chloro-1,2,3,4-tetrahydro-2-hydroxy-1α-isopropyl-2β-naphthaleneethanol, m.p. 99°–100°, 6,7-dimethoxy-1,2,3,4-tetrahydro-2-hydroxy-1α-isopropyl-2β-naphthaleneethanol, b.p. 170°/13 Pa, 1,2,3,4-tetrahydro-2-hydroxy-1α-isopropyl-5,6,7-trimethoxy-2β-naphthaleneethanol, m.p. 96°–97°, 1α-butyl-6-fluoro-1,2,3,4-tetrahydro-2-hydroxy-2β-naphthaleneethanol and

[1S,2S]-6-fluoro-1,2,3,4-tetrahydro-2-hydroxy-1-isopropyl-2-naphthaleneethanol, m.p. 78°–80°, $[\alpha]_D^{20} = +83°$ (c=1, methanol).

(D) 1,2,3,4-Tetrahydro-2-hydroxy-1α-isopropyl-2β-naphthaleneethanol was prepared as follows:

10.0 g of 6-chloro-1,2,3,4-tetrahydro-2-hydroxy-1α-isopropyl-2β-naphthaleneethanol and 4.5 g of triethylamine in 150 ml of methanol were hydrogenated at room temperature and atmospheric pressure in the presence of 1.9 g of 5% palladium-on-carbon. The filtered reaction solution was evaporated and the residue was purified by column chromatography (silica gel, hexane/ethyl acetate 1:1). After recrystallization from ethyl acetate/hexane there were obtained 1,2,3,4-tetrahydro-2-hydroxy-1α-isopropyl-2β-naphthaleneethanol, m.p. 103°–104°.

The 6-fluoro-3,4-dihydro-1-isopropyl-2(1H)-naphthalenone used as the starting material in paragraph (C) above was prepared as follows:

50 g of 2-(p-fluorophenyl)-3-methylbutyric acid were dissolved in 200 ml of benzene and treated with 54.2 g of thionyl chloride. The mixture was stirred at 60° for 45 minutes and subsequently heated to reflux for 2 hours. After evaporation of the solvent the residue was distilled, whereby 2-(4-fluorophenyl)-3-methyl-butyryl chloride, b.p. 70°/93 Pa, was obtained.

79 g of this acid chloride were dissolved in 2.7 l of methylene chloride and cooled to −10°. A stream of ethylene gas was conducted into the solution for 1 hour. 122.4 g of anhydrous aluminum chloride were then added and ethylene gas was conducted in for a further 15 minutes. The mixture was stirred at 0° for 1 hour and then treated slowly with 900 ml of water, whereby the temperature was held below 25°. The organic phase was washed with 1 l of 3N aqueous hydrochloric acid and 1 l of saturated aqueous sodium bicarbonate solution, dried over magnesium sulfate and evaporated. The product was purified by fractional distillation in vacuo. There was obtained 6-fluoro-3,4-dihydro-1-isopropyl-2(1H)-naphthalenone, b.p. 100°–105°/53 Pa.

The following compounds were obtained in an analogous manner to that described above by reaction of the corresponding acid chlorides with ethylene and aluminum chloride:

6-Chloro-3,4-dihydro-1-isopropyl-2(1H)-naphthalenone, b.p. 100°/40 Pa, 3,4-dihydro-6,7-dimethoxy-1-isopropyl-2(1H)-naphthalenone, m.p. 78°–79°, 3,4-dihydro-1-isopropyl-5,6,7-trimethoxy-2(1H)-naphthalenone, b.p. 140°/13 Pa, 1-butyl-6-fluoro-3,4-dihydro-2(1H)-naphthalenone, b.p. 110°–112°/67 Pa and

[1S]-6-fluoro-3,4-dihydro-1-isopropyl-2(1H)-naphthalenone, $[\alpha]_D^{20} = -188°$ (c=1, hexane).

EXAMPLE 2

The 6,7-dimethoxy-1,2,3,4-tetrahydro-2-hydroxy-1α-isopropyl-2β-naphthaleneethanol referred to in Example 1(C) was also prepared in the following manner:

22.0 g of 3,4-dihydro-6,7-dimethoxy-2(1H)-naphthalenone were dissolved in 300 ml of dimethylformamide and treated with 13 g of potassium tert.-butylate. The solution was stirred at 18° for 30 minutes. After the addition of 19.7 g of isopropyl iodide the mixture was stirred for a further 30 minutes, whereby the temperature was held below 30°, and then poured into water. The product was extracted with ether, the extract was washed with water, dried over magnesium sulfate and evaporated. The oil which remained behind was purified by column chromatography (silica gel, hexane/ethyl acetate 6:1). There was obtained 3,4-dihydro- 6,7-dimethoxy-1-isopropyl-2(1H)-naphthalenone, m.p. 77°-79°.

A third of a solution of 28.0 g of 3,4-dihydro-6,7-dimethoxy-1-isopropyl-2(1H)-naphthalenone and 20.9 g of ethyl bromoacetate in 180 ml of toluene/benzene 1:1 was added to 8.3 g of activated zinc dust.

After heating to reflux for a few minutes an exothermic reaction set in. The remainder of the solution was then added dropwise within 10 minutes. After completion of the addition the reaction mixture was heated to reflux for 1 hour, thereafter cooled and partitioned between 300 ml of benzene and 250 ml of 3N aqueous sulfuric acid. The organic phase was washed with water and saturated sodium bicarbonate solution and evaporated. The oily residue was dissolved in 300 ml of methanol, treated with 20 g of sodium hydroxide in 150 ml of water and the mixture was heated to reflux for 1 hour. The solution was then diluted with 1.6 l of water and the neutral constituents were extracted with 900 ml of ether. The aqueous phase was made acid with hydrochloric acid and the product was extracted in 1200 ml of ether. The extract was dried over magnesium sulfate and evaporated. Recrystallization from toluene yielded 6,7-dimethoxy-1,2,3,4-tetrahydro-2-hydroxy-1α-isopropyl-2β-naphthaleneacetic acid, m.p. 99°-101°.

16.9 g of 6,7-dimethoxy-1,2,3,4-tetrahydro-2-hydroxy-1α-isopropyl-2β-naphthaleneacetic acid were dissolved in 175 ml of tetrahydrofuran. 17.6 ml of a 10M solution of borane-methyl sulfide complex in tetrahydrofuran were added dropwise at 20° within 30 minutes. The reaction mixture was stirred at room temperature for 48 hours. After the addition of 50 ml of methanol the solution was evaporated. The residue was taken up in 300 ml of methanol and heated to reflux for 3 hours. The oil which remained behind after evaporation of the methanol was purified by column chromatography (silica gel, chloroform/methanol 40:1) and subsequently distilled under reduced pressure. There was obtained 6,7-dimethoxy-1,2,3,4-tetrahydro-2-hydroxy-1α-isopropyl-2β-naphthaleneethanol, b.p. 180°/27 Pa.

EXAMPLE 3

19.8 g of 2-[2-[(3,4-dimethoxyphenethyl)methylamino]ethyl]-6-fluoro-1,2,3,4-tetrahydro-1α-isopropyl-2α-naphthalenol were dissolved in 140 ml of chloroform and cooled to 0°. 10.0 g of methoxyacetyl chloride were added and the mixture was stirred at 0° for 3 hours. The reaction solution was poured into 500 ml of ice-cold 1N aqueous sodium hydroxide solution, the organic phase was washed with water, dried over magnesium sulfate and evaporated. The residue was dissolved in ethyl acetate, treated with an excess of hydrogen chloride in ether and again evaporated. The amorphous residue was dissolved in ethyl acetate, treated with ether, seeded and stirred at room temperature overnight. The crystallizate was filtered off, washed with ether and dried. There was obtained 2-[2-[(3,4-dimethoxyphenethyl)methylamino]ethyl]-6-fluoro-1,2,3,4-tetrahydro-1α-isopropyl-2α-naphthyl methoxyacetate hydrochloride, m.p. 150°-152°.

The following compounds were obtained in an analogous manner to that described above by reaction of the corresponding 1,2,3,4-tetrahydro-2-naphthalenol derivatives with carboxylic acid chlorides:

6-Chloro-2-[2-[(3,4-dimethoxyphenethyl)methylamino]ethyl]-1,2,3,4-tetrahydro-1α-isopropyl-2α-naphthyl methoxyacetate hydrochloride, m.p. 177°-180°, 2-[2-[(3,4-dimethoxyphenethyl)methylamino]ethyl]-1,2,3,4-tetrahydro-1α-isopropyl-2α-naphthyl methoxyacetate hydrochloride, m.p. 176°-178°, 6,7-dimethoxy-2-[2-[(3,4-dimethoxyphenethyl)methylamino]ethyl]-1,2,3,4-tetrahydro-1α-isopropyl-2α-naphthyl methoxyacetate hydrochloride, m.p. 183°-186°, 2-[2-[(3,4-dimethoxyphenethyl)methylamino]ethyl]-1,2,3,4-tetrahydro-1α-isopropyl-5,6,7-trimethoxy-2α-naphthyl methoxyacetate hydrochloride, m.p. 162°-164°, 6,7-dimethoxy-2-[2-[(3-/3,4-dimethoxyphenyl/propyl)methylamino]ethyl]-1,2,3,4-tetrahydro-1α-isopropyl-2α-naphthyl methoxyacetate hydrochloride, m.p 148°-150°, 6-fluoro-1,2,3,4-tetrahydro-1α-isopropyl-2-[2-[(2,4,6-trimethoxyphenethyl)methylamino]ethyl]-2α-naphthyl methoxyacetate hydrochloride, m.p. 138°-140°, 6-fluoro-1,2,3,4-tetrahydro-1α-isopropyl-2-[2-[(3,4,5-trimethoxyphenethyl)methylamino]ethyl]-2α-naphthyl methoxyacetate hydrochloride, m.p. 157°-159°, 2-[2-[(2,5-dimethoxyphenethyl)methylamino]ethyl]-6-fluoro-1,2,3,4-tetrahydro-1α-isopropyl-2α-naphthyl methoxyacetate hydrochloride, m.p. 161°-163°, 6-fluoro-1,2,3,4-tetrahydro-1α-isopropyl-2-[2-[(2-/2,2,2-trifluoroethoxy/phenethyl)methylamino]ethyl]-2α-naphthyl methoxyacetate hydrochloride, m.p. 169°-171°, 6-fluoro-1,2,3,4-tetrahydro-1α-isopropyl-2-[2-[(3-(2,2,2-trifluoroethoxy)phenethyl)methylamino]ethyl]-2α-naphthyl methoxyacetate hydrochloride, m.p. 167°-169°, 6-fluoro-1,2,3,4-tetrahydro-1α-isopropyl-2-[2-[(3-methoxy-4-(methylthio)phenethyl)methylamino]ethyl]-2α-naphthyl methoxyacetate hydrochloride, m.p. 157°-159°, 6-fluoro-2-[2-[(4-fluorophenethyl)methylamino]ethyl]-1,2,3,4-tetrahydro-1α-isopropyl-2α-naphthyl methoxyacetate hydrochloride, m.p. 193°-195°, 1α-butyl-2-[2-[(3,4-dimethoxyphenethyl)methylamino]ethyl]-6-fluoro-1,2,3,4-tetrahydro-2α-naphthyl methoxyacetate hydrochloride, m.p. 108°-110°, 6-fluoro-1,2,3,4-tetrahydro-1α-isopropyl-2-[2-[(4-methoxyphenethyl)methylamino]ethyl]-2α-naphthyl methoxyacetate hydrochloride, m.p. 204°-206°, 2-[2-[(4-butoxyphenethyl)methylamino]ethyl]-6-fluoro-1,2,3,4-tetrahydro-1α-isopropyl-2α-naphthyl methoxyacetate hydrochloride, m.p. 134°-135°, 2-[2-[(4-decyloxyphenethyl)methylamino]ethyl]-6-fluoro-1,2,3,4-tetrahydro-1α-isopropyl-2α-naphthyl methoxyacetate hydrochloride, m.p. 105°-106°, 2-[2-[(3,4-dimethoxyphenethyl)methylamino]ethyl]-6-fluoro-1,2,3,4-tetrahydro-1α-isopropyl-2α-naphthyl ethylcarbonate hydrochloride, m.p. 94°-97°, 2-[2-[(3,4-dimethoxyphenethyl)methylamino]ethyl]-6-fluoro-1,2,3,4-tetrahydro-1α-isopropyl-2α-naphthyl(2-methoxyethyl)carbonate hydrochloride, m.p. 113°-115°, 2-[2-[(3,4-dimethoxyphenethyl)methylamino]ethyl]-6-fluoro-1,2,3,4-tetrahydro-1α-isopropyl-2α-naphthyl (methylthio)acetate hydrochloride, m.p. 110°-112°, 2-[2-[(3,4-dimethoxyphenethyl)methylamino]ethyl]-6-fluoro-1,2,3,4-tetrahydro-1α-isopropyl-2α-naphthyl (4-methoxyphenyl)acetate hydrochloride, m.p. 129°-131°, 6,7-dimethoxy-2-[2-[(3,4-dimethoxyphenethyl)methylamino]ethyl]-1,2,3,4-tetrahydro-1α-isopropyl-2α-naphthyl butyrate, m.p. 104°–106° and

[1S,2S]-2-[2-[(3,4-dimethoxyphenethyl)methylamino]ethyl]-6-fluoro-1,2,3,4-tetrahydro-1-isopropyl-2-naphthylmethoxyacetate hydrochloride, m.p. 175°–176°, $[\alpha]_D^{20} = +35.2°$ (c=1, methanol).

EXAMPLE 4

3.97 g of 2-(6,7-dimethoxy-1,2,3,4-tetrahydro-2-hydroxy-1α-isopropyl-2β-naphthyl)ethyl p-toluenesulfonate and 3.96 g of 4-[(3,4-dimethoxyphenyl)butyl]methylamine were dissolved in 7 ml of dimethyl sulfoxide and stirred at 80° for 1 hour. The reaction mixture was partitioned between ethyl acetate and water and the organic phase was washed with water, dried over magnesium sulfate and concentrated. The product, purified by column chromatography (silica gel, chloroform/methanol 25:1), was converted into the hydrochloride as described above. There was obtained 6,7-dimethoxy-2-[2-[[4-(3,4-dimethoxyphenyl)butyl]methylamino]ethyl]-1,2,3,4-tetrahydro-1α-isopropyl-2α-naphthalenol hydrochloride, m.p. 137°–139°.

The following compounds were obtained in an analogous manner to that described above by condensation of certain of the substituted 2-(1,2,3,4-tetrahydro-2-hydroxy-1α-isopropyl-2β-naphthyl)ethyl p-toluenesulfonates set forth in Example 1 with the corresponding N-methyl-arylalkylamines:

6-Fluoro-1,2,3,4-tetrahydro-1α-isopropyl-2-[2-[(phenethyl)methylamino]ethyl]-2α-naphthalenol hydrochloride, m.p. 176°–177°, 6,7-dimethoxy-1,2,3,4-tetrahydro-1α-isopropyl-2-[2-[[4-methoxy-3-(3-methoxypropoxy)phenethyl]methylamino]ethyl]-2α-naphthalenol and 6,7-dimethoxy-1,2,3,4-tetrahydro-1α-isopropyl-2-[2-[[3-methoxy-4-(3-methoxypropoxy)phenethyl]methylamino]ethyl]-2α-naphthalenol.

EXAMPLE 5

A solution of 2.3 g of 6,7-dimethoxy-2-[2-[[4-(3,4-dimethoxyphenyl)butyl]methylamino]ethyl]-1,2,3,4-tetrahydro-1α-isopropyl-2α-naphthalenol in 20 ml of acetic anhydride was stirred at room temperature for 16 hours. The reaction mixture was added to 200 ml of ice-water, made alkaline with 28% aqueous sodium hydroxide solution and the product was extracted with ethyl acetate. The extract was washed with water, dried over magnesium sulfate and evaporated. The residue was dissolved in ethyl acetate, treated with an excess of hydrogen chloride in ether and again evaporated. The amorphous residue was dissolved in ethyl acetate, treated with ether and stirred for 2 hours. The crystallizate formed was filtered off, washed with ether and dried. There was obtained 6,7-dimethoxy-2-[2-[[4-(3,4-dimethoxyphenyl)butyl]methylamino]ethyl]-1,2,3,4-tetrahydro-1α-isopropyl-2α-naphthyl acetate hydrochloride, m.p. 143°–145°.

The following compounds were obtained in an analogous manner to that described above by reaction of the corresponding 1,2,3,4-tetrahydro-2-naphthalenol derivatives with acetic anhydride:

6-Chloro-2-[2-[(3,4-dimethoxyphenethyl)methylamino]ethyl]-1,2,3,4-tetrahydro-1α-isopropyl-2α-naphthyl acetate hydrochloride, m.p. 172°–174°, 2-[2-[(3,4-dimethoxyphenethyl)methylamino]ethyl]-1,2,3,4-tetrahydro-1α-isopropyl-2α-naphthyl acetate hydrochloride, m.p. 184°–185°, 6,7-dimethoxy-2-[2-[(3,4-dimethoxyphenethyl)methylamino]ethyl]-1,2,3,4-tetrahydro-1α-isopropyl-2α-naphthyl acetate hydrochloride, m.p. 194°–196°, 2-[2-[(3,4-dimethoxyphenethyl)methylamino]ethyl]-1,2,3,4-tetrahydro-1α-isopropyl-5,6,7-trimethoxy-2α-naphthyl acetate hydrochloride (amorphous), 6,7-dimethoxy-2-[2-[[3-(3,4-dimethoxyphenyl)propyl]methylamino]ethyl]-1,2,3,4-tetrahydro-1α-isopropyl-2α-naphthyl acetate hydrochloride, m.p. 151°–153°, 6-fluoro-1,2,3,4-tetrahydro-1α-isopropyl-2-[2-[(2,4,6-trimethoxyphenethyl)methylamino]ethyl]-2α-naphthyl acetate hydrochloride, m.p. 159°–161°, 6-fluoro-1,2,3,4-tetrahydro-1α-isopropyl-2-[2-[(2-(2,2,2-trifluoroethoxy)phenethyl)methylamino]ethyl]-2α-naphthyl acetate hydrochloride, m.p. 152°–154°, 6-fluoro-1,2,3,4-tetrahydro-1α-isopropyl-2-[2-[(3-(2,2,2-trifluoroethoxy)phenethyl)methylamino]ethyl]-2α-naphthyl acetate hydrochloride, m.p. 163°–165°, 1α-butyl-2-[2-[(3,4-dimethoxyphenethyl)methylamino]ethyl]-6-fluoro-1,2,3,4-tetrahydro-2α-naphthyl acetate hydrochloride, m.p. 117°–119°, 6-fluoro-1,2,3,4-tetrahydro-1α-isopropyl-2-[2-[(phenethyl)methylamino]ethyl]-2α-naphthyl acetate hydrochloride, m.p. 225°–227°, 2-[2-[(3,4-dimethoxyphenethyl)methylamino]ethyl]-6-fluoro-1,2,3,4-tetrahydro-1α-isopropyl-2α-naphthyl acetate hydrochloride, m.p. 169°–171°, 6,7-dimethoxy-1,2,3,4-tetrahydro-1α-isopropyl-2-[2-[[4-methoxy-3-(3-methoxypropoxy)phenethyl]methylamino]ethyl]-2α-naphthyl acetate hydrochloride, m.p. 143°–145° and 6,7-dimethoxy-1,2,3,4-tetrahydro-1α-isopropyl-2-[2-[[3-methoxy-4-(3-methoxypropoxy)phenethyl]methylamino]ethyl]-2α-naphthyl acetate hydrochloride, m.p. 136°–138°.

EXAMPLE 6

(A) 17.0 g of 2-(5,8-dimethoxy-1,2,3,4-tetrahydro-2-hydroxy-2-naphthyl)ethyl p-toluenesulfonate and 16.3 g of N-methylhomoveratrylamine were heated to 100° for 30 minutes. The reaction mixture was partitioned between ethyl acetate and water, and the organic phase was dried over magnesium sulfate and evaporated. After purification by column chromatography (silica gel, chloroform/methanol 40:1) there was obtained 5,8-di-methoxy-2-[2-[(3,4-dimethoxyphenethyl)methylamino]ethyl]-1,2,3,4-tetrahydro-2-naphthalenol which was converted into the hydrochloride, m.p. 156°–158°.

In an analogous manner, from 2-(6,7-dimethoxy-1,2,3,4-tetrahydro-2-hydroxy-2-naphthyl)ethyl p-toluenesulfonate there was obtained 6,7-dimethoxy-2-[2-[(3,4-dimethoxyphenethyl)-methylamino]ethyl]-1,2,3,4-tetrahydro-2-naphthalenol hydrochloride, m.p. 175°–177°.

The 2-(5,8-dimethoxy-1,2,3,4-tetrahydro-2-hydroxy-2-naphthyl)ethyl p-toluenesulfonate used as the starting material in paragraph (A) above was prepared as follows:

(B) 11.5 g of 5,8-dimethoxy-1,2,3,4-tetrahydro-2-hydroxy-2-naphthaleneethanol were dissolved in 70 ml of pyridine and treated with 10.5 g of p-toluenesulfonyl chloride. The mixture was stirred at 0° for 16 hours and then poured into 500 ml of water. The product was extracted in 500 ml of ether, the extract was washed with 0.5N aqueous hydrochloric acid and saturated aqueous sodium bicarbonate solution and dried over magnesium sulfate. After evaporation 2-(5,8-dimethoxy-1,2,3,4-tetrahydro-2-hydroxy-2-naphthyl)ethyl p-toluenesulfonate remained behind.

In an analogous manner, by the selective tosylation of 6,7-dimethoxy-1,2,3,4-tetrahydro-2-hydroxy-2-naphthaleneethanol there was obtained 2-(6,7-dimethoxy-1,2,3,4-tetrahydro-2-hydroxy-2-naphthyl)ethyl p-toluenesulfonate.

The 5,8-dimethoxy-1,2,3,4-tetrahydro-2-hydroxy-2-naphthaleneethanol used as the starting material in paragraph (B) above was prepared as follows:

(C) 15.5 g of 5,8-dimethoxy-1,2,3,4-tetrahydro-2-hydroxy-2-naphthaleneacetic acid in 150 ml of tetrahydrofuran were added dropwise within 15 minutes to 3.32 g of lithium aluminum hydride in 150 ml of tetrahydrofuran. The reaction mixture was heated to reflux for 1 hour and then cooled. After the dropwise addition of 15 ml of ethyl acetate and 20 ml of water the suspension was filtered and the filtrate was concentrated. The product was purified by column chromatography (silica gel, chloroform/methanol 30:1). There was obtained 5,8-dimethoxy-1,2,3,4-tetrahydro-2-hydroxy-2-naphthaleneethanol, m.p. 121°–122°.

In an analogous manner, by the reduction of 6,7-dimethoxy-1,2,3,4-tetrahydro-2-hydroxy-2-naphthaleneacetic acid there was obtained 6,7-dimethoxy-1,2,3,4-tetra-hydro-2-hydroxy-2-naphthaleneethanol, m.p. 91°–93°.

(D) The 5,8-dimethoxy-1,2,3,4-tetrahydro-2-hydroxy-2-napthaleneacetic acid used as the starting material in paragraph (C) above was prepared as follows:

A fifth of a solution of 20.6 g of 3,4-dihydro-5,8-dimethoxy-2(1H)-naphthalenone and 18.4 g of ethyl bromoacetate in 100 ml of toluene/benzene (1:1) was added to 7.4 g of activated zinc dust. An exothermic reaction set in after heating to reflux for a few minutes. The remainder of the solution was then added dropwise within 10 minutes. The reaction mixture was then heated to reflux for 1½ hours, cooled and partitioned between 300 ml of benzene and 300 ml of 3N aqueous sulfuric acid. The organic phase was washed with water and saturated aqueous sodium bicarbonate solution and evaporated. The residue was dissolved in 200 ml of methanol, treated with a solution of 10 g of sodium hydroxide in 100 ml of water and the mixture was heated to reflux for 3 hours. The solution was concentrated to half of the volume, treated with 500 ml of water and the neutral constituents were extracted with 500 ml of chloroform. The aqueous phase was made acid with sulfuric acid and the product was extracted in 900 ml of ether. The extract was dried over magnesium sulfate and evaporated. Recrystallization of the residue yielded 5,8-dimethoxy-1,2,3,4-tetrahydro-2-hydroxy-2-naphthaleneacetic acid, m.p. 112°–114°.

In an analogous manner, by the reaction of 3,4-dihydro-6,7-dimethoxy-2(1H)-naphthalenone with zinc/ethyl bromoacetate and subsequent saponification there was obtained 6,7-dimethoxy-1,2,3,4-tetrahydro-2-hydroxy-2-naphthaleneacetic acid, m.p. 100°–102°.

EXAMPLE 7

(A) 4.3 g of 5,8-dimethoxy-2-[2-[(3,4-dimethoxyphenethyl)methylamino]ethyl]-1,2,3,4-tetrahydro-2-naphthalenol were dissolved in 15 ml of acetic anhydride and stirred at room temperature for 18 hours. The reaction mixture was poured into water, made alkaline with sodium hydroxide solution and the product was extracted in chloroform. The solvent was evaporated and the residue was dissolved in ethyl acetate, treated with an excess of hydrogen chloride in ether and again evaporated. Crystallization of the amorphous residue from ethyl acetate yielded 5,8-dimethoxy-2-[2-[(3,4-dimethoxyphenethyl)methylamino]ethyl]-1,2,3,4-tetrahydro-2-naphthyl acetate hydrochloride, m.p. 115°–117°.

In an analogous manner, by the acetylation of 6,7-dimethoxy-2-[2-[(3,4-dimethoxyphenethyl)methylamino]ethyl]-1,2,3,4-tetrahydro-2-naphthalenol there was obtained 6,7-dimethoxy-2-[2-[(3,4-dimethoxyphenethyl)methylamino]ethyl]-1,2,3,4-tetrahydro-2-naphthyl acetate hydrochloride, m.p. 162°–164°.

EXAMPLE 8

A mixture of 2.0 g of 6,7-dimethoxy-1,2,3,4-tetrahydro-2-hydroxy-1α-isopropyl-2β-naphthalenepropionaldehyde, 1.51 g of N-methylhomoveratrylamine hydrochloride and 0.33 g of triethylamine in 35 ml of methanol was treated with 0.41 g of sodium cyanoborohydride and stirred at room temperature for 2 hours. After the addition of 3.5 ml of 36% hydrochloric acid the reaction mixture was evaporated and the residue was partitioned between 50 ml of 3N aqueous sodium hydroxide solution and 100 ml of ether. The organic phase was evaporated and the product was purified by column chromatography (silica gel, chloroform/methanol 20:1). There was obtained 6,7-dimethoxy-2-[3-[(3,4-dimethoxyphenethyl)methylamino]propyl]-1,2,3,4-tetrahydro-1α-isopropyl-2α-naphthalenol, m.p. 97°–99°.

The 6,7-dimethoxy-1,2,3,4-tetrahydro-2-hydroxy-1α-isopropyl-2β-naphthalenepropionaldehyde used as the starting material was prepared as follows:

2.8 g of 6,7-dimethoxy-1,2,3,4-tetrahydro-2-hydroxy-1α-isopropyl-2β-naphthalenepropionitrile were dissolved in 50 ml of methylene chloride and cooled to 0°. There were now added dropwise at this temperature within 10 minutes 10 ml of a 1.2M solution of diisobutylaluminum hydride in toluene and the mixture was subsequently stirred at room temperature for 2 hours. There were then added thereto in succession 4 ml of methanol, 2.2 ml of water and 5 ml of methanol, the suspension was stirred for 30 minutes and filtered. The filtrate was concentrated and the product was purified by column chromatography (silica gel, hexane/ethyl acetate 1:2). After recrystallization from cyclohexane there was obtained 6,7-dimethoxy-1,2,3,4-tetrahydro-2-hydroxy-1α-isopropyl-2β-naphthalenepropionaldehyde, m.p. 133°–135°. The spectroscopic data (Nuclear Magnetic Resonance and Infra-Red Spectra) show that the substance was present as the hemiacetal.

The above-named 6,7-dimethoxy-1,2,3,4-tetrahydro-2-hydroxy-1α-isopropyl-2β-naphthalenepropionitrile used as the starting material was prepared as follows:

1.6 g of sodium cyanide were dissolved in 20 ml of dimethyl sulfoxide at 100° and cooled to 40°. 7.3 g of 2-(6,7-dimethoxy-1,2,3,4-tetrahydro-2-hydroxy-1α-isopropyl-2β-naphthyl)ethyl p-toluene-sulfonate in 10 ml of dimethyl sulfoxide were added thereto. The mixture was stirred at room temperature for 2 days and subsequently partitioned between 200 ml of water and 200 ml of ether. The organic phase was washed with water and evaporated, and the residue was purified by column chromatography (silica gel, hexane/ethyl acetate 4:1). There was obtained 6,7-dimethoxy-1,2,3,4-tetrahydro-2-hydroxy-1α-isopropyl-2β-napthalenepropionitrile, m.p. 82°–83°.

EXAMPLE 9

1.1 g of 6,7-dimethoxy-2-[3-[(3,4-dimethoxyphenethyl)methylamino]propyl]-1,2,3,4-tetrahydro-1α-isopropyl-2α-naphthalenol were dissolved in 15 ml of acetic anhydride and the solution was stirred at 70° for 20 hours. The reaction mixture was poured on to ice-water, made alkaline with sodium hydroxide solution and the product was extracted in ethyl acetate. The evaporated extract was purified by column chromatography (silica gel, chloroform/methanol 25:1) and the product was converted into the hydrochloride. There was obtained 6,7-dimethoxy-2-[3-[(3,4-dimethoxyphenethyl)methylamino]propyl]-1,2,3,4-tetrahydro-1α-isopropyl-2α-naphthyl acetate hydrochloride, m.p. 145°–147°.

EXAMPLE A

| Tablets Composition: | |
|---|---|
| (1) 2-[2-[(3,4-Dimethoxyphenethyl)methylamino]ethyl]-6-fluoro-1,2,3,4-tetrahydro-1α-isopropyl-2α-naphthyl methoxyacetate hydrochloride | 75 mg |
| (2) Lactose powder | 135 mg |
| (3) Maize starch white | 55 mg |
| (4) Polyvinylpyrrolidone | 15 mg |
| (5) Maize starch white | 15 mg |
| (6) Talc | 3 mg |
| (7) Magnesium stearate | 2 mg |
| Tablet weight | 300 mg |

Manufacturing procedure:

1–3 are mixed intensively. The mixture is thereafter moistened with an aqueous solution of 4 and kneaded, and the resulting mass is granulated, dried and sieved. The granulate is mixed with 5–7 and pressed to tablets of suitable size.

EXAMPLE B

| Tablets Composition: | | |
|---|---|---|
| (1) 2-[2-[(3,4-Dimethoxyphenethyl)methylamino]ethyl]-6-fluoro-1,2,3,4-tetrahydro-1α-isopropyl-2α-naphthyl methoxyacetate hydrochloride | 75 mg | 60 mg |
| (2) Lactose powder | 100 mg | 100 mg |
| (3) Maize starch | 60 mg | 60 mg |
| (4) Polyvinylpyrrolidone | 5 mg | 5 mg |
| (5) Maize starch | 15 mg | 15 mg |
| (6) Sodium carboxymethylstarch | 5 mg | 5 mg |
| (7) Talc | 3 mg | 3 mg |
| (8) Magnesium stearate | 2 mg | 2 mg |
| Tablet weight | 265 mg | 250 mg |

Manufacturing procedure:

1–3 are mixed intensively. The mixture is thereafter moistened with an aqueous solution of 4 and kneaded, and the resulting mass is granulated, dried and sieved. The granulate is mixed with 5–7 and pressed to tablets of suitable size.

EXAMPLE C

| Tablets Composition: | | |
|---|---|---|
| (1) 2-[2-[(3,4-dimethoxyphenethyl)methylamino]ethyl]-6-fluoro-1,2,3,4-tetrahydro-1α-isopropyl-2α-naphthyl methoxyacetate hydrochloride | 75 mg | 90 mg |
| (2) Lactose powder | 46 mg | 46 mg |
| (3) Cellulose microcrystalline | 60 mg | 60 mg |
| (4) Polyvinylpyrrolidone | 10 mg | 10 mg |
| (5) Sodium carboxymethylstarch | 4 mg | 4 mg |
| (6) Talc | 3 mg | 3 mg |
| (7) Magnesium stearate | 2 mg | 2 mg |
| Tablet weight | 200 mg | 215 mg |

Manufacturing procedure:

1–3 are mixed intensively. The mixture is thereafter moistened with an aqueous solution of 4 and kneaded, and the resulting mass is granulated, dried and sieved. The granulate is mixed with 5–7 and pressed to tablets of suitable size.

EXAMPLE D

| Capsules Composition: | |
|---|---|
| (1) 2-[2-[(3,4-Dimethoxyphenethyl)methylamino]ethyl]-6-fluoro-1,2,3,4-tetrahydro-1α-isopropyl-2α-naphthyl methoxyacetate hydrochloride | 75 mg |
| (2) Lactose crystals | 100 mg |
| (3) Maize starch white | 20 mg |
| (4) Talc | 9 mg |
| (5) Magnesium stearate | 1 mg |
| Capsule fill weight | 205 mg |

Manufacturing procedure:

The active substance is mixed intensively with the lactose. This mixture is thereafter admixed with the maize starch, the talc and the magnesium stearate, and the mixture is filled into capsules of suitable size.

EXAMPLE E

| Capsules Composition | |
|---|---|
| (1) 2-[2-[(3,4-Dimethoxyphenethyl)methylamino]ethyl]-6-fluoro-1,2,3,4-tetrahydro-1α-isopropyl-2α-naphthyl methoxyacetate hydrochloride | 75 mg |
| (2) Cellulose microcrystalline | 100 mg |
| (3) Sodium carboxymethylstarch | 5 mg |
| (4) Talc | 9 mg |
| (5) Magnesium stearate | 1 mg |
| Capsule fill weight | 190 mg |

Manufacturing procedure:

The active substance is mixed intensively with the cellulose. This mixture is thereafter admixed with the sodium carboxymethylstarch, the talc and the magnesium stearate and the mixture is filled into capsules of suitable size.

EXAMPLE F

| Injection solution | 1 ml |
|---|---|
| 2-[2-[(3,4-Dimethoxyphenethyl)methylamino]-6-fluoro-1,2,3,4-tetrahydro-1α-isopropyl-2α-naphthyl | 8 mg |

| Injection solution | |
|---|---|
| | 1 ml |
| methoxyacetate hydrochloride | |
| Sodium chloride crystals pure | 8.5 mg |
| Water for injection | ad 1 ml |

EXAMPLE G

When the procedures described in Examples A–F are followed, tablets, capsules and injection preparations can be manufactured from the following, likewise preferred compounds:

[1S,2S]-2-[2-[(3,4-Dimethoxyphenethyl)methylamino]ethyl]-6-fluoro-1,2,3,4-tetrahydro-1-isopropyl-2-naphthyl methoxyacetate hydrochloride.

6,7-Dimethoxy-2-[2-[(3,4-dimethoxyphenethyl)methylamino]ethyl]-1,2,3,4-tetrahydro-1α-isopropyl-2α-naphthyl methoxyacetate hydrochloride.

6,7-Dimethoxy-2-[2-[(3,4-dimethoxyphenethyl)methylamino]ethyl]-1,2,3,4-tetrahydro-1α-isopropyl-2α-naphthyl acetate hydrochloride.

We claim:

1. A compound of the formula

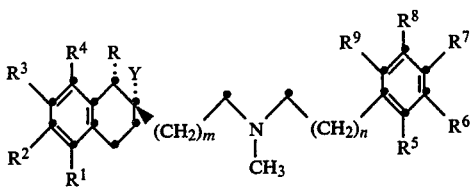

I wherein R is hydrogen of lower-alkyl, $R^1$, $R^2$, $R^3$ and $R^4$ each independently is hydrogen, halogen or lower-alkoxy or two of $R^1$, $R^2$, $R^3$ and $R^4$ on adjacent carbon atoms taken together are methylenedioxy or ethylenedioxy, $R^5$, $R^6$, $R^7$, $R^8$ and $R^9$ each independently is hydrogen, halogen, $C_1$–$C_{10}$-alkoxy, lower alkylthio, lower-alkoxy-lower alkoxy or $\omega,\omega,\omega$-trifluoro-lower alkoxy or two of $R^5$, $R^6$, $R^7$, $R^8$ and $R^9$ on adjacent carbon atoms taken together are methylenedioxy or ethylenedioxy, Y is hydroxy, lower-alkylcarbonyloxy, lower-alkoxy-lower-alkylcarbonyloxy, lower-alkoxycarbonyloxy, lower-alkoxy-lower-alkoxycarbonyloxy, lower-alkylthio-lower-alkylcarbonyoxy or benzylcarbonyloxy optionally mono- or di-substituted on the benzene ring by lower-alkyl, lower-alkoxy, halogen or nitro, m is the number 1 or 2 and n is the number 1, 2 or 3, its optical antipode, or a racemate thereof, or a pharmaceutically acceptable acid addition salt thereof.

2. A compound in accordance with claim 1, wherein R is lower-alkyl.

3. A compound in accordance with claim 2, wherein R is isopropyl.

4. A compound in accordance with claim 1, wherein Y is hydroxy, lower-alkyl-carbonyloxy or lower-alkoxy-lower-alkylcarbonyloxy.

5. A compound in accordance with claim 4, wherein Y is hydroxy, acetoxy or methoxyacetoxy.

6. A compound in accordance with claim 1, wherein m and n each is the number 1.

7. A compound in accordance with claim 1, wherein two of the substituents $R^1$, $R^2$, $R^3$ and $R^4$ are hydrogen and the other two each independently is hydrogen, halogen or lower-alkoxy.

8. A compound in accordance with claim 7, wherein $R^1$ and $R^4$ each is hydrogen and $R^2$ and $R^3$ each is lower-alkoxy or $R^2$ is halogen and $R^3$ is hydrogen.

9. A compound in accordance with claim 1, wherein two of the substituents $R^5$, $R^6$, $R^7$, $R^8$ and $R^9$ are hydrogen and the other three each independently is hydrogen, halogen, $C_1$–$C_{10}$-alkoxy, lower-alkylthio or lower-alkoxy-lower-alkoxy.

10. A compound in accordance with claim 9, wherein $R^5$ is hydrogen or $C_1$–$C_{10}$-alkoxy, $R^6$ is hydrogen, $C_1$–$C_{10}$-alkoxy or lower-alkoxy-lower-alkoxy, $R^7$ is hydrogen, halogen, $C_1$–$C_{10}$-alkoxy, lower-alkylthio or lower-alkoxy-lower-alkoxy and $R^8$ and $R^9$ each is hydrogen.

11. A compound in accordance with claim 1, wherein R is isopropyl, Y is hydroxy, acetoxy or methoxyacetoxy, $R^1$, $R^4$, $R^8$ and $R^9$ each is hydrogen, $R^2$ and $R^3$ each is lower-alkoxy or $R^2$ is halogen and $R^3$ is hydrogen, $R^5$ is hydrogen or $C_1$–$C_{10}$-alkoxy, $R^6$ is hydrogen, $C_1$–$C_{10}$-alkoxy or lower-alkoxy-lower-alkoxy, $R^7$ is hydrogen, halogen, $C_1$–$C_{10}$-alkoxy, lower-alkylthio or lower-alkoxy-lower-alkoxy and m and n each is the number 1.

12. A compound in accordance with claim 1, 2-[2-[(3,4-dimethoxyphenethyl)methylamino]ethyl]-6-fluoro-1,2,3,4-tetrahydro-1α-isopropyl-2α-naphthyl methoxyacetate, or a pharmaceutically acceptable acid addition salt thereof.

13. A compound in accordance with claim 1, 6,7-dimethoxy-2-[2-[(3,4-dimethoxyphenethyl)methylamino]ethyl]-1,2,3,4-tetrahydro-1α-isopropyl-2α-naphthyl methoxyacetate or a pharmaceutically acceptable acid addition salt thereof.

14. A compound in accordance with claim 1, 6,7-dimethoxy-2-[2-[(3,4-dimethoxyphenethyl)methylamino]ethyl]-1,2,3,4-tetrahydro-1α-isopropyl-2α-naphthyl acetate or a pharmaceutically acceptable acid addition salt thereof.

15. A compound in accordance with claim 1, [1S,2S]-2-[2-[(3,4-dimethoxyphenethyl)methylamino]ethyl]-6-fluoro-1,2,3,4-tetrahydro-1-isopropyl-2-naphthyl methoxyacetate, or its racemate, or a pharmaceutically acceptable acid addition salt thereof.

16. A compound in accordance with claim 15, [1S,2S]-2-[2-[(3,4-dimethoxyphenethyl)methylamino]ethyl]-6-fluoro-1,2,3,4-tetrahydro-1-isopropyl-2-naphthyl methoxyacetate, or a pharmaceutically acceptable acid addition salt thereof.

17. A compound in accordance with claim 1, [1R,2R]-2-[2-[(3,4-dimethoxyphenethyl)methylamino]ethyl]-6-fluoro-1,2,3,4-tetrahydro-1-isopropyl-2-naphthyl methoxy acetate or a pharmaceutically acceptable acid addition salt thereof.

18. A compound of the formula

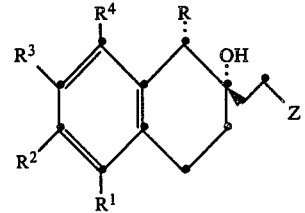

wherein R is hydrogen or lower-alkyl, $R^1$, $R^2$, $R^3$ and $R^4$ each independently is hydrogen, halogen or lower-alkoxy or two of $R^1$, $R^2$, $R^3$ and $R^4$ on adjacent carbon atoms taken together are methylenedioxy or ethylenedioxy and Z is hydroxy, hydroxymethyl, formyl, cyano, halogen, arylsulfonyloxy, alkylsulfonyloxy or the group —CH$_2$—X in which X is, halogen, arylsulfonyloxy or alkylsulfonyloxy.

19. A compound in accordance with claim 18, wherein R is lower-alkyl.

20. A compound in accordance with claim 19, 2-(6-fluoro-1,2,3,4-tetrahydro-2-hydroxy-1α-isopropyl-2β-naphthyl)ethyl p-toluenesulfonate.

21. A compound of the formula

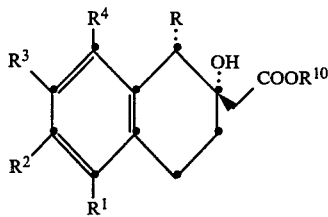

VI wherein R is hydrogen or lower-alkyl, $R^1$, $R^2$, $R^3$ and $R^4$ each independently is hydrogen, halogen or lower-alkoxy or two of $R^1$, $R^2$, $R^3$ and $R^4$ on adjacent carbon atoms taken together are methylenedioxy or ethylenedioxy and $R^{10}$ is hydrogen or lower-alkyl.

22. A compound in accordance with claim 21, wherein R is lower-alkyl.

23. A compound in accordance with claim 22, 6,7-dimethoxy-1,2,3,4-tetrahydro-2-hydroxy-1α-isopropyl-2β-naphthaleneacetic acid.

24. A composition for controlling high blood pressure containing an effective amount of a compound of the formula:

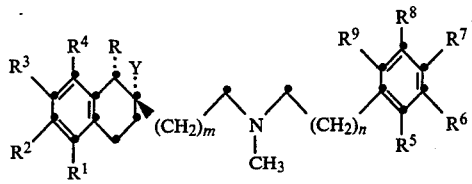

I wherein R is hydrogen or lower-alkyl, $R^1$, $R^2$, $R^3$ and $R^4$ each independently is hydrogen, halogen or lower-alkoxy or two of $R^1$, $R^2$, $R^3$ and $R^4$ on adjacent carbon atoms taken together are methylenedioxy or ethylenedioxy, $R^5$, $R^6$, $R^7$, $R^8$ and $R^9$ each independently is hydrogen, halogen, $C_1$-$C_{10}$-alkoxy, lower alkylthio, lower-alkoxy-lower-alkoxy or ω,ω, ω-trifluoro-lower-alkoxy or two of $R^5$, $R^6$, $R^7$, $R^8$ and $R^9$ on adjacent carbon atoms taken together are methylenedioxy or ethylenedioxy, Y is hydroxy, lower-alkylcarbonyloxy, lower-alkoxy-lower-alkylcarbonyloxy, lower-alkoxycarbonyloxy, lower-alkoxy-lower-alkoxycarbonyloxy, lower-alkylthio-lower-alkyl-carbonyloxy or benzylcarbonyloxy optionally mono- or di-substituted on the benzene ring by lower-alkyl, lower-alkoxy, halogen or nitro, m is the number 1 or 2 and n is the number 1, 2 or 3, its optical antipode or a racemate thereof or a pharmaceutically acceptable acid addition salt thereof, and a pharmaceutically acceptable carrier material.

25. A composition in accordance with claim 24, wherein R is lower-alkyl.

26. A composition in accordance with claim 25, wherein the compound of formula I is [1S,2S]-2-[2-[(3,4-dimethoxyphenethyl)methylamino]ethyl]-6-fluoro-1,2,3,4-tetrahydro-1-isopropyl-2-naphthyl methoxyacetate or its racemate, or a pharmaceutically acceptable acid addition salt thereof.

27. A composition in accordance with claim 26, wherein the compound of formula I is [1S,2S]-2-[2-[(3,4-dimethoxyphenethy)methylamino]ethyl]-6-fluoro-1,2,3,4-tetrahydro-1-isopropyl-2-naphthyl methoxyacetate, or a pharmaceutically acceptable acid addition salt thereof.

28. A method for controlling high blood pressure which comprises administering to a warm blooded animal in need of such treatment an effective amount of a compound of the formula

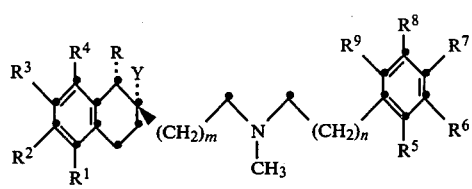

I wherein R is hydrogen or lower-alkyl, $R^1$, $R^2$, $R^3$ and $R^4$ each independently is hydrogen, halogen or lower-alkoxy or two of $R^1$, $R^2$, $R^3$ and $R^4$ on adjacent carbon atoms taken together are methylenedioxy or ethylenedioxy, $R^5$, $R^6$, $R^7$, $R^8$ and $R^9$ each independently is hydrogen, halogen, $C_1$-$C_{10}$-alkoxy, lower alkythio, lower-alkoxy-lower-alkoxy or ω,ω,ω-trifluoro-lower-alkoxy or two of $R^5$, $R^6$, $R^7$, $R^8$, and $R^9$ on adjacent carbon atoms taken together are methylenedioxy or ethylenedioxy. Y is hydroxy, lower-alkylcarbonyloxy, lower-alkoxy-lower-alkylcarbonyloxy, lower-alkoxycarbonyloxy, lower-alkoxy-lower-alkoxy-carbonyloxy, lower-alkylthio-lower alkylcarbonyloxy or benzylcarbonyloxy optionally mono- or di-substituted on the benzene ring by lower-alkyl, lower-alkoxy, halogen or nitro, m is the number 1 or 2 and n is the number 1, 2 or 3, its optical antipode, or a racemate thereof or a pharmaceutically acceptable acid addition salt thereof.

29. A method in accordance with claim 28, wherein R is lower-alkyl.

30. A method in accordance with claim 29, wherein the compound of formula I is [1S,2S]-2-[2-[(3,4-dimethoxyphenethyl)methylamino]ethyl]-6-fluoro-1,2,3,4-tetrahydro-1-isopropyl-2-naphthyl methoxyacetate or its racemate, or a pharmaceutically acceptable acid addition salt thereof.

31. A method in accordance with claim 30 wherein the compound of formula I is [1S,2S]-2-[2-[(3,4-dimethoxyphenethyl)methylamino]ethyl]-6-fluoro-1,2,3,4]-tetrahydo-1-isopropyl-2-naphthylmethoxyacetate or a pharmaceutically acceptable acid addition salt thereof.

32. A method of producing calcium-antagonistic effects which comprises administering to a warm blooded animal in need of such treatment an effective amount of a compound of the formula

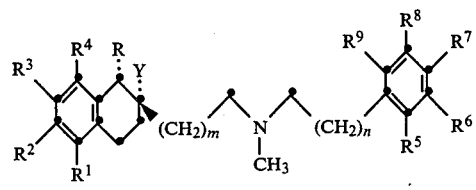

I wherein R is hydrogen or lower-alkyl, $R^1$, $R^2$, $R^3$ and $R^4$ each independently is hydrogen, halogen or lower-alkoxy or two of $R^1$, $R^2$, $R^3$ and $R^4$ on adjacent carbon atoms taken together are methylenedioxy or ethylenedioxy, $R^5$, $R^6$, $R^7$, $R^8$ and $R^9$ each independently is hydrogen, halogen, $C_1$–$C_{10}$-alkoxy, lower alkylthio, lower-alkoxy-lower-alkoxy or $\omega,\omega,\omega$-trifluoro-lower-alkoxy or two of $R^5$, $R^6$, $R^7$, $R^8$ and $R^9$ on adjacent carbon atoms taken together are methylenedioxy or ethylenedioxy, Y is hydroxy, lower-alkylcarbonyloxy, lower-alkoxy-lower-alkylcarbonyloxy, lower-alkoxy-carbonyloxy, lower-alkoxy-lower-alkoxycarbonyloxy, lower-alkyl-thio-lower-alkyl-carbonyloxy or benzyl-carbonyloxy optionally mono- or di-substituted on the benzene ring by lower-alkyl, lower-alkoxy, halogen or nitro m is the number 1 or 2 and n is the number 1, 2 or 3, its optical antipode, or a racemate thereof or a pharmaceutically acceptable acid addition salt thereof.

33. A method in accordance with claim 32, wherein R is lower-alkyl.

34. A method in accordance with claim 33, wherein the compound of formula I is [1S,2S]-2-[2-[(3,4-dimethoxyphenethyl)methylamino]ethyl]-6-fluoro-1,2,3,4-tetrahydro-1-isopropyl-2-naphthyl methoxyacetate or its racemate, or a pharmaceutically acceptable acid addition salt thereof.

35. A method in accordance with claim 34 wherein the compound of formula I is [1S,2S]-2-[2-[(3,4-dimethoxyphenethyl)methylamino]ethyl]-6-fluoro-1,2,3,4-tetrahydro-1-isopropyl-2-naphthyl methoxyacetate or a pharmaceutically acceptable acid addition salt thereof.

36. A compound in accordance with claim 18, wherein Z is chlorine, bromine, tosyloxy, bromobenzenesulfonyloxy, benzenesulfonyloxy, mesitylenesulfonyloxy, mesyloxy, or trifluoromethylsulfonyloxy.

* * * * *